(12) United States Patent  (10) Patent No.: US 8,979,856 B2
Catanzarite et al.  (45) Date of Patent: Mar. 17, 2015

(54) PATIENT-SPECIFIC PARTIAL KNEE GUIDES AND OTHER INSTRUMENTS

(71) Applicant: Materialise NV, Leuven (BE)

(72) Inventors: Joshua B. Catanzarite, Warsaw, IN (US); Ryan J. Schoenefeld, Fort Wayne, IN (US); Louis J. Keppler, Valley City, OH (US)

(73) Assignee: Materialise NV, Leuven (BE)

( * ) Notice: Subject to any disclaimer, the term of this patent is extended or adjusted under 35 U.S.C. 154(b) by 0 days.

(21) Appl. No.: 14/073,792

(22) Filed: Nov. 6, 2013

(65) Prior Publication Data

US 2014/0066938 A1 Mar. 6, 2014

Related U.S. Application Data

(63) Continuation of application No. PCT/US2012/041893, filed on Jun. 11, 2012.

(60) Provisional application No. 61/496,177, filed on Jun. 13, 2011.

(51) Int. Cl.
*A61B 17/58* (2006.01)
*A61B 17/60* (2006.01)
*A61F 2/00* (2006.01)
*A61B 17/17* (2006.01)
*A61B 17/15* (2006.01)
*A61B 17/56* (2006.01)
*A61F 2/38* (2006.01)

(52) U.S. Cl.
CPC .......... *A61B 17/1764* (2013.01); *A61B 17/157* (2013.01); *A61B 2017/568* (2013.01); *A61F 2002/3895* (2013.01)
USPC .......................................................... 606/88

(58) Field of Classification Search
CPC ....................................................... A61B 17/155
USPC ................................................................ 606/88
See application file for complete search history.

(56) References Cited

U.S. PATENT DOCUMENTS

| | | | | |
|---|---|---|---|---|
| 5,364,402 A | * | 11/1994 | Mumme et al. | 606/88 |
| 5,387,216 A | * | 2/1995 | Thornhill et al. | 606/88 |
| 6,033,410 A | * | 3/2000 | McLean et al. | 606/88 |
| 8,728,086 B2 | * | 5/2014 | Smith et al. | 606/88 |
| 8,764,760 B2 | * | 7/2014 | Metzger et al. | 606/88 |
| 8,777,875 B2 | * | 7/2014 | Park | 600/587 |
| 2009/0024131 A1 | | 1/2009 | Metzger et al. | |
| 2010/0305573 A1 | * | 12/2010 | Fitz et al. | 606/87 |
| 2011/0071533 A1 | | 3/2011 | Metzger et al. | |

OTHER PUBLICATIONS

International Search Report on WO/2012/173929 published Oct. 23, 2012 (Application No. PCT/US2012/041893 filed Jun. 11, 2012).

* cited by examiner

*Primary Examiner* — David Bates
(74) *Attorney, Agent, or Firm* — EIP US LLP

(57) ABSTRACT

A surgical kit for unicompartmental knee arthroplasty includes a unitary patient-specific unicompartmental tibial guide and a tibial drill template and other instruments. The tibial guide has a patient-specific body with an inner surface preoperatively configured to nestingly conform and mate in only one position with an anterior portion and a proximal portion of one compartment of a tibial bone of a specific patient. The tibial guide includes a drill guide portion preoperatively configured for drilling first and second anterior holes into the tibial bone for guiding a horizontal tibial resection. The tibial guide includes a vertical resection guide portion preoperatively configured for guiding a vertical resection through the tibial bone before the horizontal resection.

17 Claims, 12 Drawing Sheets

PATIENT-SPECIFIC PARTIAL KNEE GUIDES AND OTHER INSTRUMENTS

CROSS-REFERENCE TO RELATED APPLICATIONS

This application is a continuation under 35 U.S.C. §120 of International Application No. PCT/US/2012/041893, filed Jun. 11, 2012 (and published in the English language as International Publication No. WO 2012/173929), which claims the benefit of U.S. Provisional Patent Application No. 61/496,177, filed Jun. 13, 2011. Each of the above-specified applications is hereby incorporated by reference in its entirety.

INTRODUCTION

The present teachings provide various patient-specific guides and other instruments for partial or unicompartmental knee arthroplasty. Various patient-specific femoral and tibial partial knee guides and drill guides are provided. The patient-specific guides are designed and constructed preoperatively based on three-dimensional digital images of the patient's knee joint and/or other joints. The digital images of the patient's joint can be reconstructed from medical scans of the patient using commercially available CAD (Computer Aided Design) and/or other imaging software.

SUMMARY

This section provides a general summary of the disclosure, and is not a comprehensive disclosure of its full scope or all of its features.

The present teachings provide a surgical kit for unicompartmental knee arthroplasty. In some embodiments, the surgical kit can include, for example, a unitary patient-specific unicompartmental tibial guide and a tibial drill template or other instruments. In some embodiments the surgical kit can include a patient-specific unicompartmental femoral guide and a femoral drill template or other instruments.

The tibial guide can have a patient-specific body with an inner surface preoperatively configured to nestingly conform and mate in only one position with an anterior portion and a proximal portion of one compartment of a tibial bone of a specific patient. The tibial guide includes a drill guide portion preoperatively configured for drilling first and second anterior holes into the tibial bone for guiding a horizontal tibial resection. The tibial guide includes a vertical resection guide portion preoperatively configured for guiding a vertical resection through the tibial bone before the horizontal resection.

The femoral guide can have a patient-specific body with an inner surface preoperatively configured to nestingly conform and mate in only one position with an anterior portion and a distal portion of one compartment of a distal femoral bone of a specific patient. The femoral guide includes an elongated slot with a tapered inner wall configured to receive a femoral drill template.

The present teachings also provide a method for unicompartmental knee arthroplasty. In some embodiments the method includes mounting a patient-specific tibial guide on a tibial bone and nestingly mating and registering a patient-specific inner surface of the tibial guide onto a corresponding anterior surface and a corresponding proximal surface of medial proximal plateau of the tibial bone. The method further includes registering a tibial drill template to the tibial guide by inserting first and second tapered registration formations of the tibial drill template into first and second tapered bores of the tibial guide. First and second holes can be drilled through the first and second registration formations into the anterior surface of the tibial bone. A vertical tibial resection of the medial proximal plateau is made through a vertical resection slot of the tibial guide. The tibial guide and tibial drill template are removed. A horizontal resection of the medial proximal plateau is made and the medial proximal plateau of the tibial bone is removed.

In some embodiments, the method includes mounting a patient-specific femoral guide on a femoral bone, and nestingly mating and registering a patient-specific inner surface of the femoral guide onto a corresponding medial anterior surface and a corresponding medial distal surface of the femoral bone. A femoral drill template is registered to the femoral guide by inserting a tapered portion of the femoral drill template into an elongated tapered slot of the femoral guide. First and second holes are drilled into the femoral bone through first and second registration holes of the femoral drill template. First and second pins are inserted into the first and second holes in the femoral bone. The femoral guide and femoral drill template are removed, a resection block is mounted on the first and second pins, and a resection of the femoral bone is made through the resection block.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
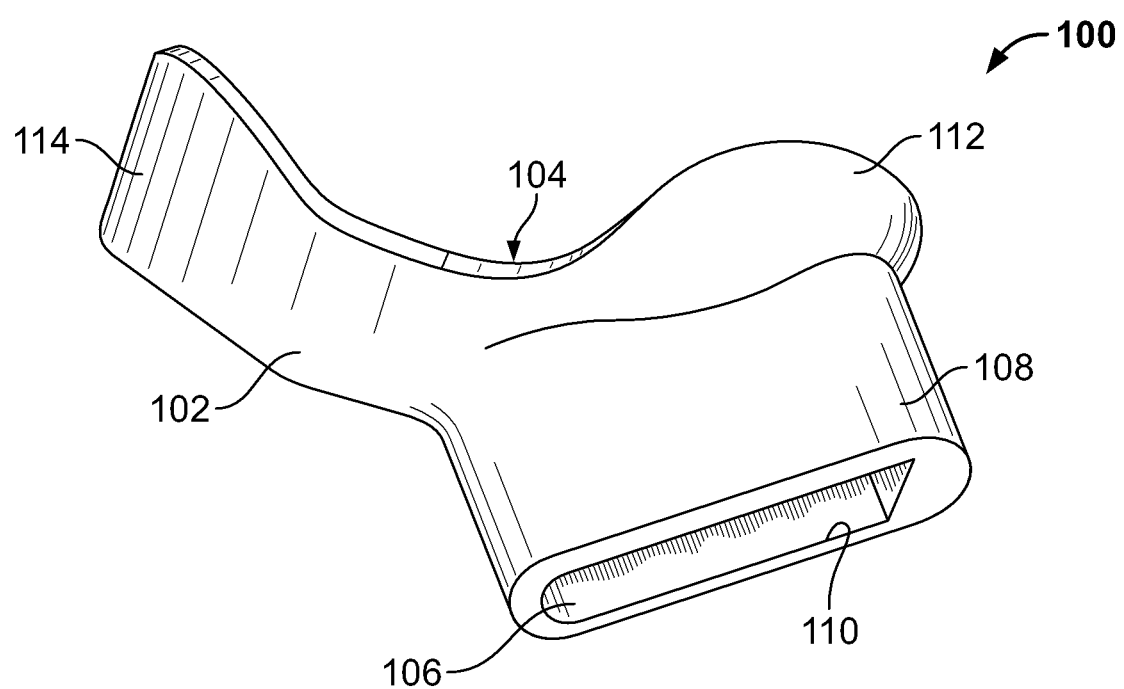
FIG. 1 is a perspective view of a patient-specific partial femoral alignment guide according to the present teachings, shown for the right knee.

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The present teachings provide various patient-specific guides and other instruments for partial or unicompartmental knee arthroplasty. Various patient-specific femoral and tibial partial knee guides and drill guides are provided. The patient-specific guides are designed and constructed preoperatively based on three-dimensional digital images of the patient's knee joint and/or other joints. The digital images of the patient's joint can be reconstructed from medical scans of the patient using commercially available CAD and/or other imaging software.

In the context of the present teachings, patient-specific devices, including alignment and/or resection guides, other patient-specific instrument components and patient-specific implants are generally configured to match the anatomy of a specific patient in one or more respects. Patient-specific devices are generally formed using computer modeling based on the patient's reconstructed three-dimensional anatomic image for the corresponding joint or other parts of the anatomy of the patient. The patient-specific devices have an engagement surface that is made to conformingly contact and match a three-dimensional image/model of the patient's bone surface (with or without cartilage or other soft tissue), by the computer-assisted image methods, as discussed below.

In this respect, patient-specific devices can nestingly mate and register in only one position with the corresponding joint surface (with or without articular cartilage) of the specific patient replicating complementarily at least a portion of the joint surface. Patient-specific alignment guides, for example, can include custom-made (patient-specific) guiding formations, such as, for example, guiding holes for sutures, K-wires or for inserting pins or other fasteners in configurations determined by a surgeon-approved pre-operative plan. In some embodiments, patient-specific alignment guides can also be configured as patient-specific resection guides and include patient-specific cutting guides, such as cutting slots or edges for guiding a cutting tool to perform preoperatively planned resections of the joint.

The patient-specific devices and other associated instruments and implants can be designed preoperatively using computer-assisted image methods based on three-dimensional images of the patient's knee anatomy reconstructed from MRI, CT, ultrasound, X-ray, or other three- or two-dimensional medical scans of the patient's anatomy and in some cases complemented with digital photography methods and/or anthropometry databases. Various CAD programs and/or software can be utilized for three-dimensional image reconstruction, such as software commercially available, for example, by Materialise US, Plymouth, Mich.

In the preoperative planning stage for arthroplasty, imaging data of the relevant anatomy of a patient can be obtained at a medical facility or doctor's office, using one of medical imaging methods described above. The imaging data can include, for example, various medical scans of a relevant portion of the patient's anatomy, as needed for joint modeling, including images of all the knee joint and, optionally, images of the femoral head or hip joint and ankle joint for mechanical axis determination. An initial preoperative plan can be prepared for the patient in image space and can include planning and determination for joint resections, custom implant design or non-custom implant selection, sizing and fitting, designing patient-specific alignment and/or resection guides for guiding the joint resections, as well as other components or tools for the surgical procedure.

Various patient-specific instruments and pre-operative planning procedures are disclosed in commonly assigned and co-pending U.S. patent application Ser. No. 11/756,057, filed on May 31, 2007, U.S. patent application Ser. No. 12/211,407, filed Sep. 16, 2008; U.S. patent application Ser. No. 11/971,390, filed on Jan. 9, 2008, U.S. patent application Ser. No. 11/363,548, filed on Feb. 27, 2006; U.S. patent application Ser. No. 12/025,414, filed Feb. 4, 2008, U.S. patent application Ser. No. 12/571,969, filed Oct. 1, 2009, and U.S. patent application Ser. No. 12/955,361, filed Nov. 29, 2010. The disclosures of the above applications are incorporated herein by reference.

The various patient-specific instrument component discussed herein can be made of any biocompatible material, including metal or plastic. Generally, the patient-specific alignment and/or resection guides can be single use, disposable and made of lightweight materials, including polymers. The various patient-specific components described herein can be manufactured by various stereolithography methods, selective laser sintering, fused deposition modeling or other rapid prototyping methods. In some embodiments, computer instructions of tool paths for machining the patient-specific guides and/or implants can be generated and stored in a tool path data file. The tool path data can be provided as input to a CNC mill or other automated machining system.

Figure 14:
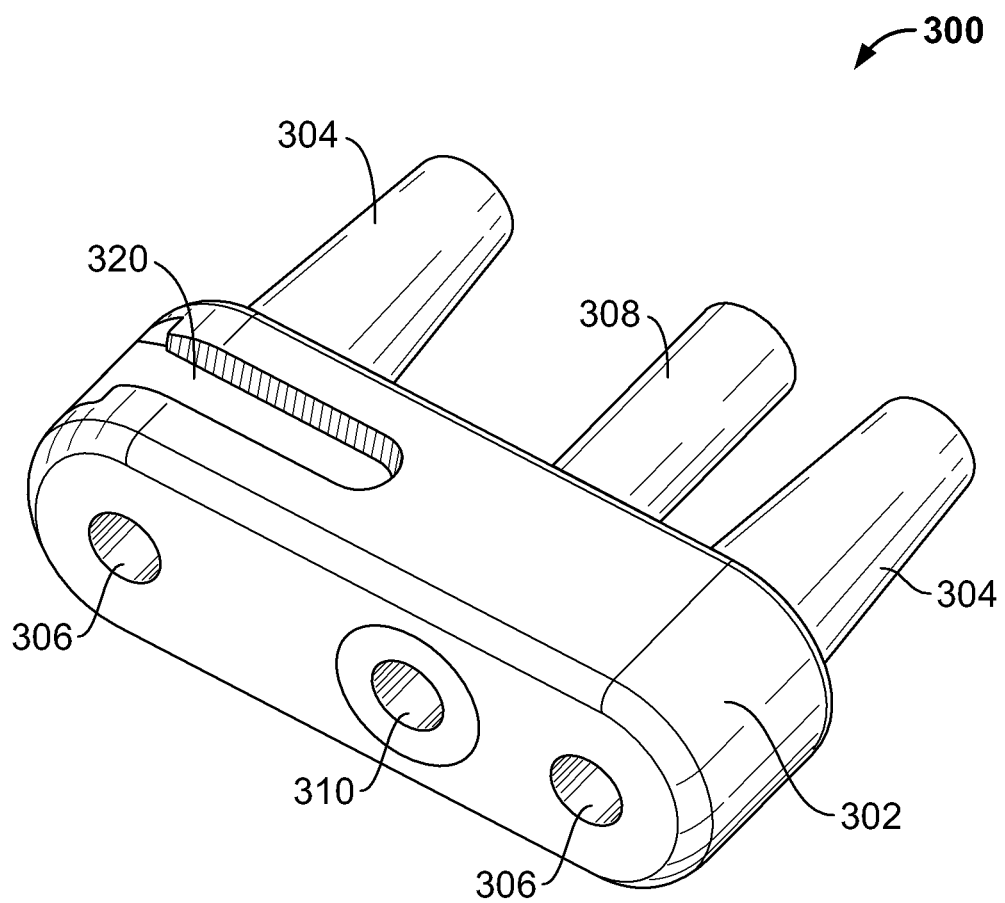
FIG. 14 is a perspective view of a tibial drill template for use with a patient-specific partial tibial guide according to the present teachings.
Figure 15:
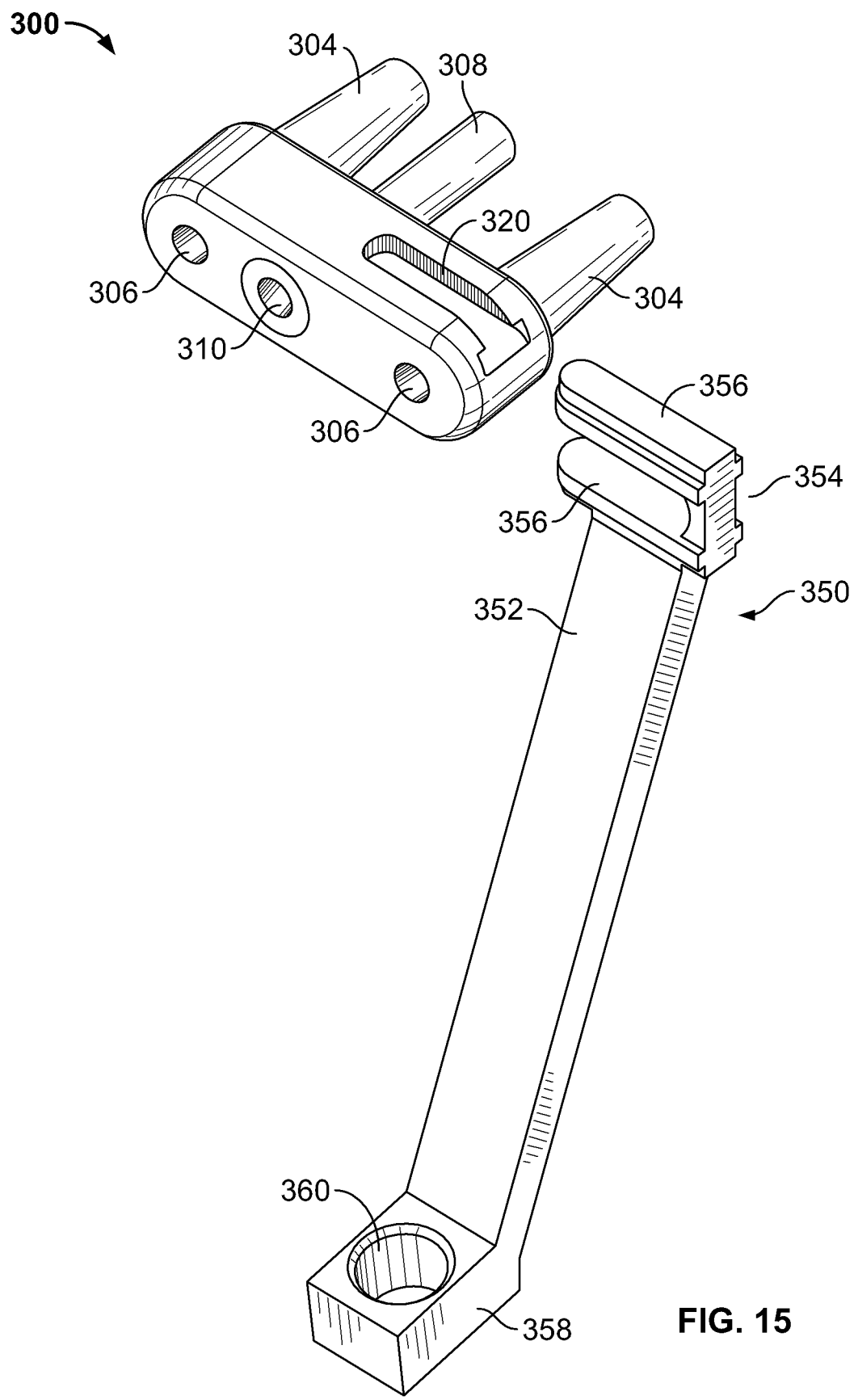
FIG. 15 is a perspective view of an alignment verification instrument shown with a tibial drill template.

Various embodiments of patient-specific femoral alignment guides for unicompartmental (or unilateral or unicondylar) knee arthroplasty for the left or the right knee are illustrated in FIGS. 1, 2 and 4-7A and referenced below as "partial" femoral alignment guides. FIGS. 7B, 7C, 7D, 8 and 8A illustrate various embodiments of femoral drill templates 120 for use with partial femoral alignment guides. FIG. 3 illustrates a resection block 150 that can be used with the femoral alignment guides. FIGS. 9-13 illustrate various embodiments of patient-specific tibial alignment/resection guides 200 for unicompartmental knee arthroplasty, referenced as "partial" tibial guides. FIGS. 14 and 15 illustrate tibial drill templates 300 and associated instruments for use with the partial tibial guides. It should be noted that although unicompartmental knee arthroplasty using the devices of the present teaching can be performed on either the lateral or medial compartments of the knee, current surgical practice is restricted to the medial compartment of the knee. Accordingly, any reference to lateral compartmental use is not an indication or endorsement of such surgical practice.

Figure 2:
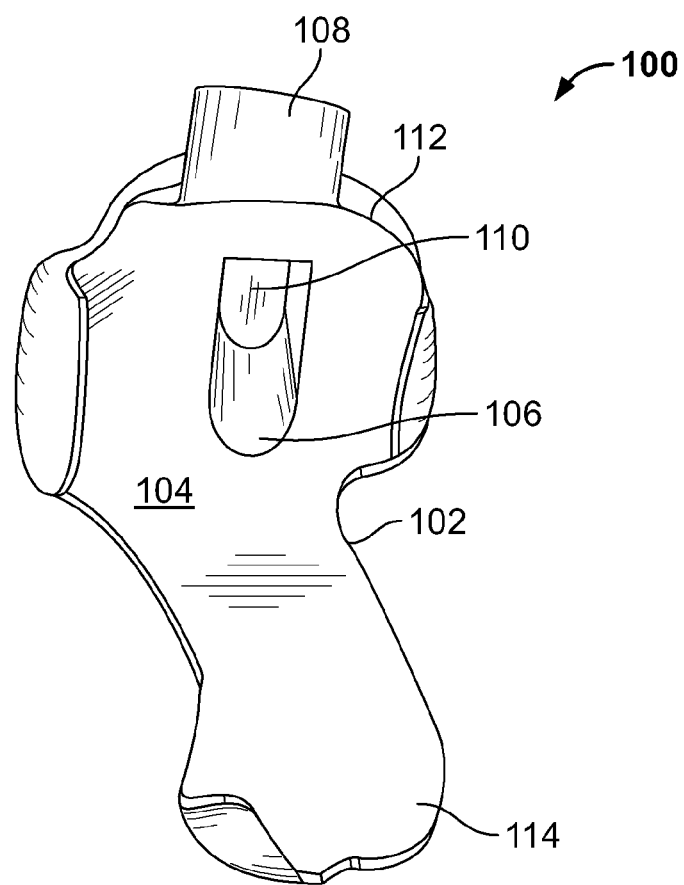
FIG. 2 is another perspective view of the patient-specific partial femoral alignment guide of FIG. 1.
Figure 3:
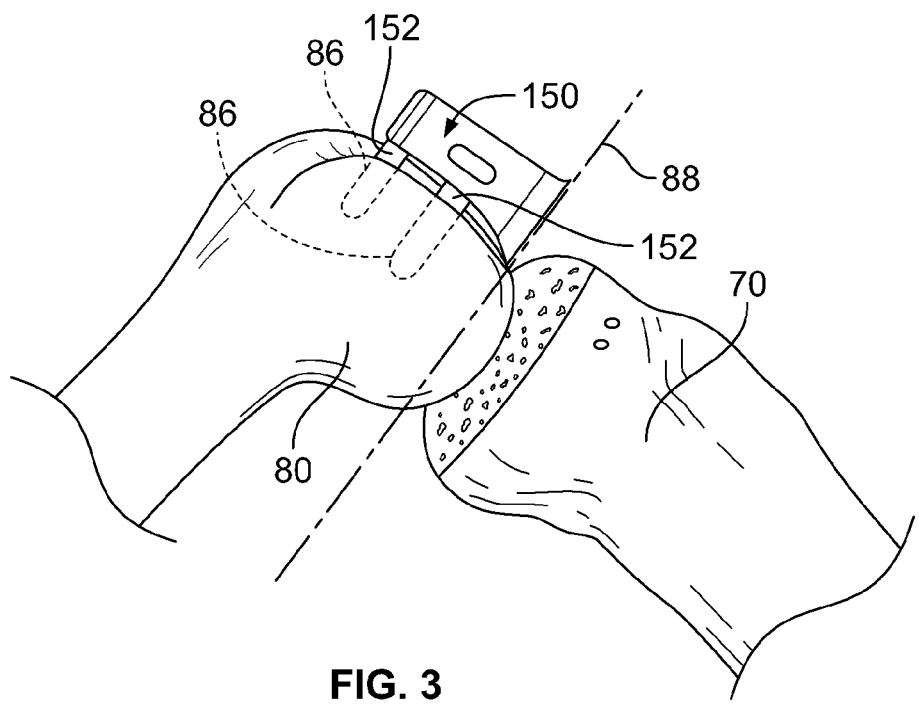
FIG. 3 is an environmental view of a femoral bone with a resection block supported in holes drilled in the bone using a patient-specific partial femoral alignment guide with a drill template according to the present teachings.
Figure 4:
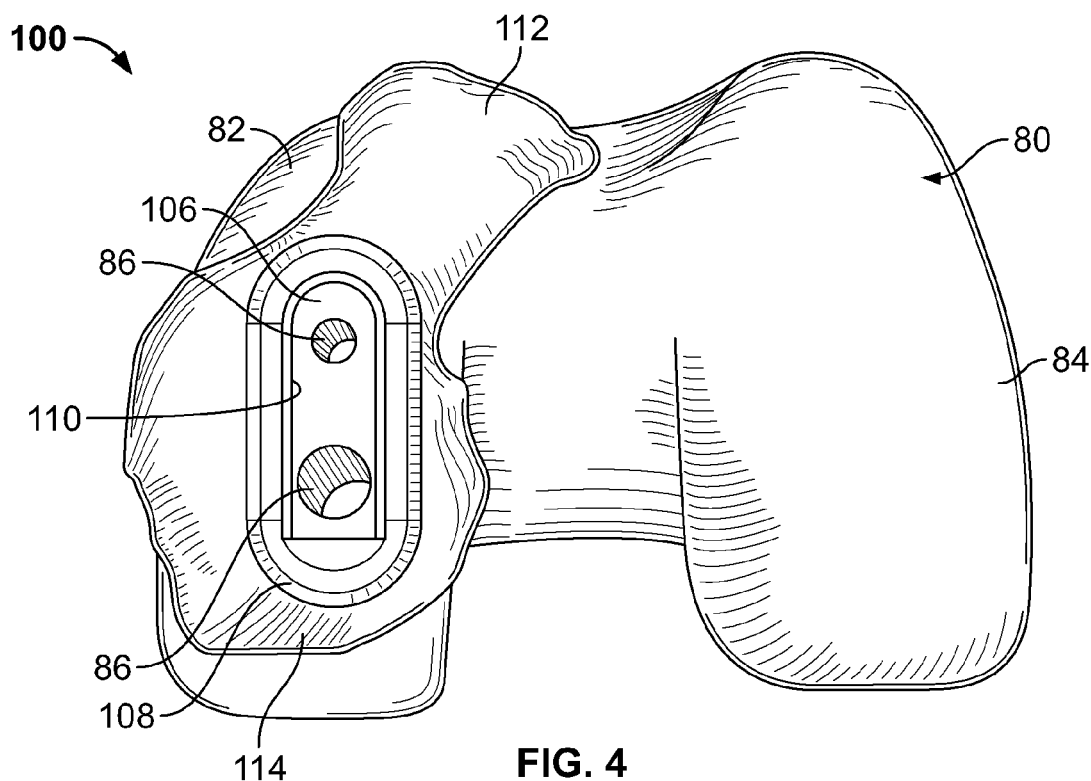
FIG. 4 is an environmental view of a patient-specific partial femoral alignment guide according to the present teachings shown for the left knee.

Referring to FIGS. 1 and 2, an exemplary partial femoral alignment guide 100 is illustrated. The partial femoral alignment guide 100 is patient-specific and includes a body 102 with a three-dimensional patient-specific undersurface or inner surface 104 designed during the preoperative plan to conform to unilaterally, i.e., to only one of the medial and lateral surfaces/femoral condyles 82, 84 of the femoral bone 80 (either with or without articular cartilage) of the patient in only one position, as shown in FIG. 4. The body 102 and the inner surface 104 can extend from a distal portion 112 over one of the lateral or medial femoral condyles to an anterior portion 114. The femoral alignment guide 100 can be marked with the name of the patient (and surgeon) and the corresponding knee and condyle, such as "RIGHT/MEDIAL", for example, for convenient preoperative and intraoperative identification. An elongated guiding formation 108 extends generally from the distal portion 112. The guiding formation 108 defines an elongated slot 106 with a tapered inner peripheral wall 110 for registering a femoral drill insert or template 120, as discussed below.

Figure 5:
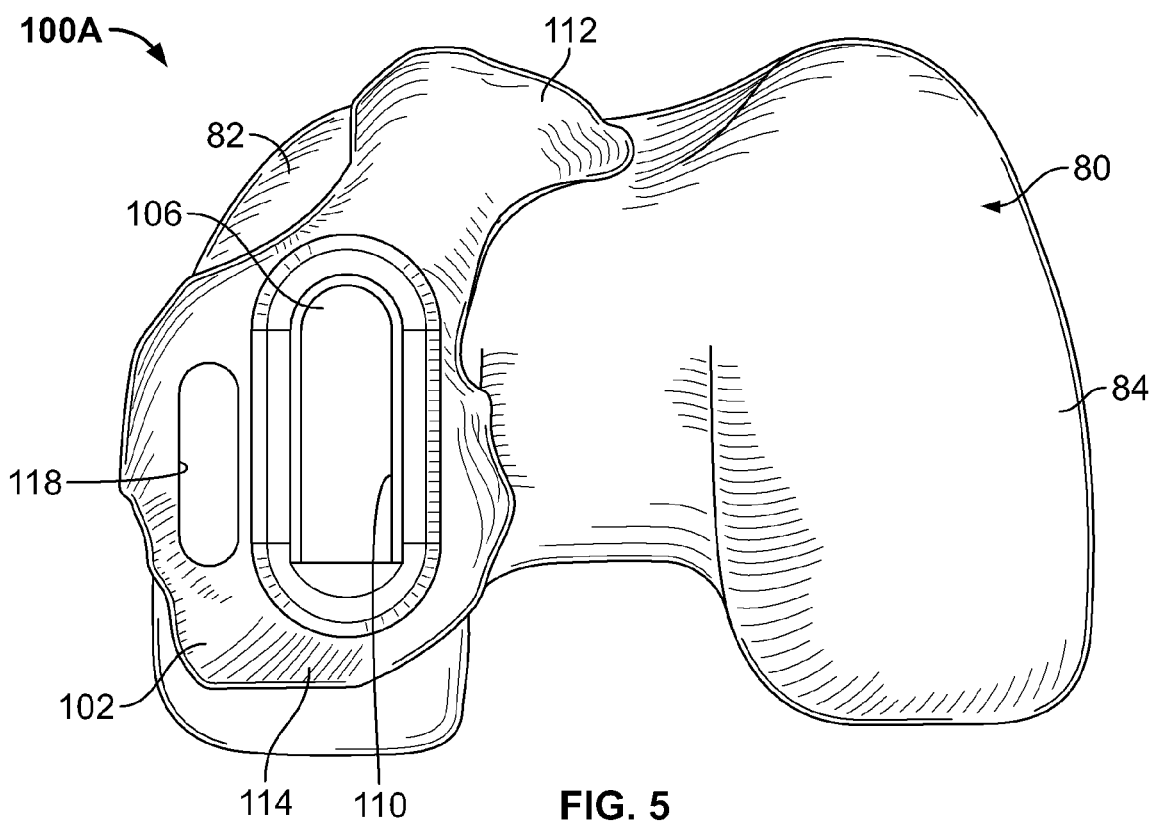
FIG. 5 is an environmental view of another patient-specific partial femoral alignment guide according to the present teachings shown for the left knee.
Figure 6:
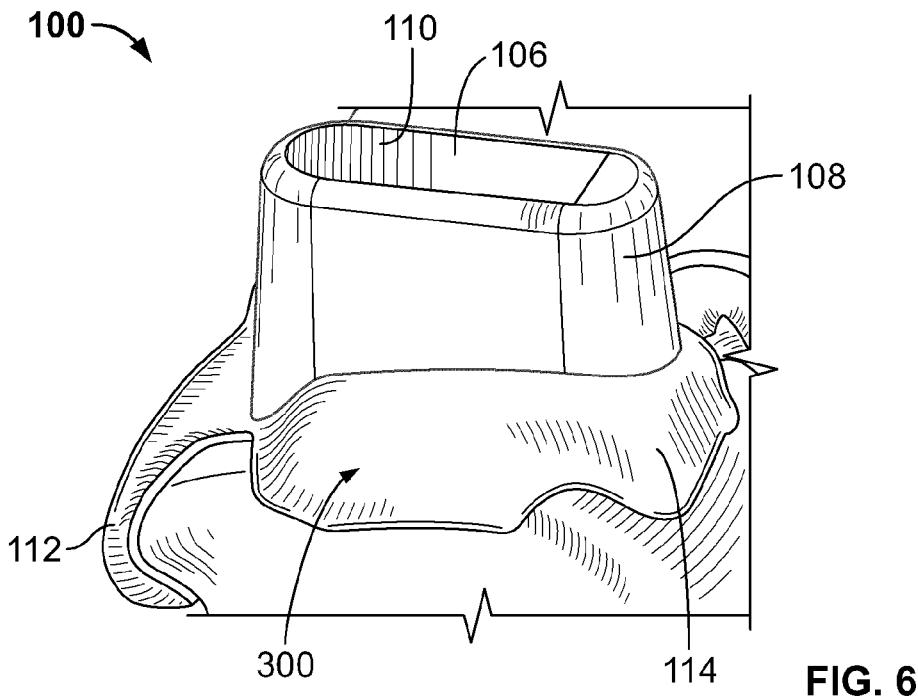
FIG. 6 is another environmental view of a patient-specific partial femoral alignment guide according to the present teachings.
Figure 7A:
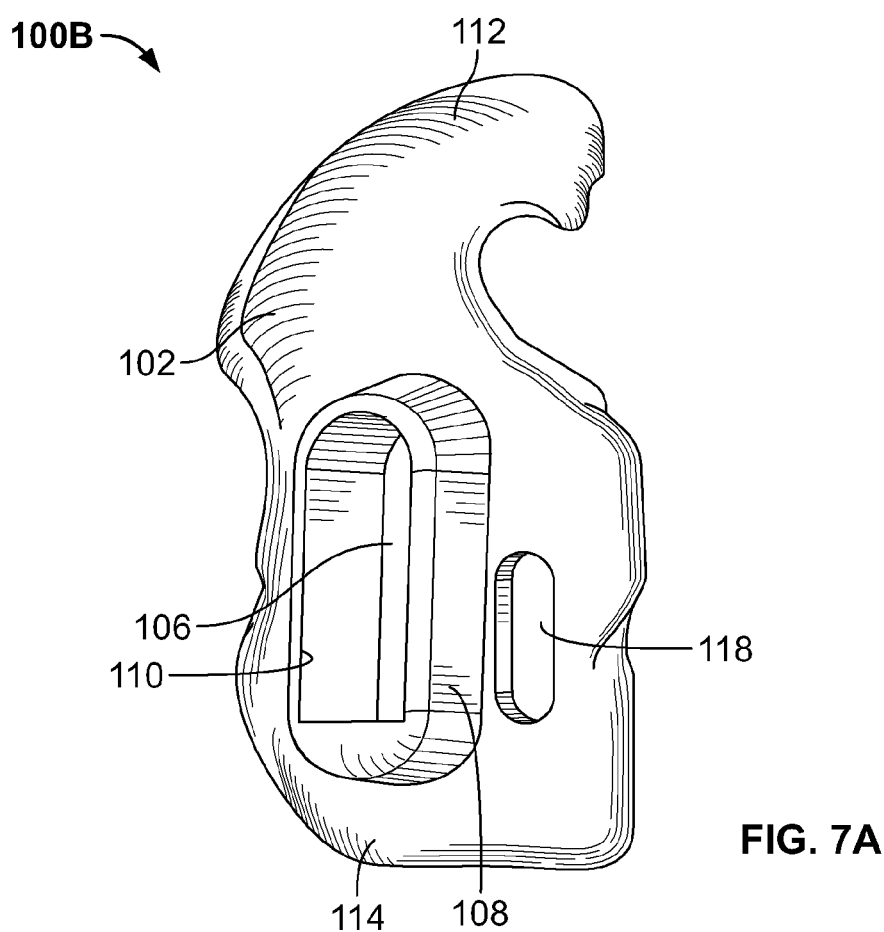
FIG. 7A is a perspective view of a patient-specific partial femoral alignment guide according to the present teachings shown for the right knee.

FIG. 4 illustrates a partial femoral alignment guide 100 for the left knee. In some embodiments, when a larger size implant is used, the partial femoral alignment guide can include a window 118, as shown in FIGS. 5 and 7A. A left-knee partial femoral alignment guide 100A with a window 118 is illustrated in FIG. 5 and a right-knee partial femoral alignment guide 100B with a window 118 is illustrated in FIG. 7A. The partial femoral alignment guides 100A, 100B are illustrated for the medial condyle 82 and the window 118 is on the medial side of the guiding formation 108.

Figures 7B, 7C, 7D:
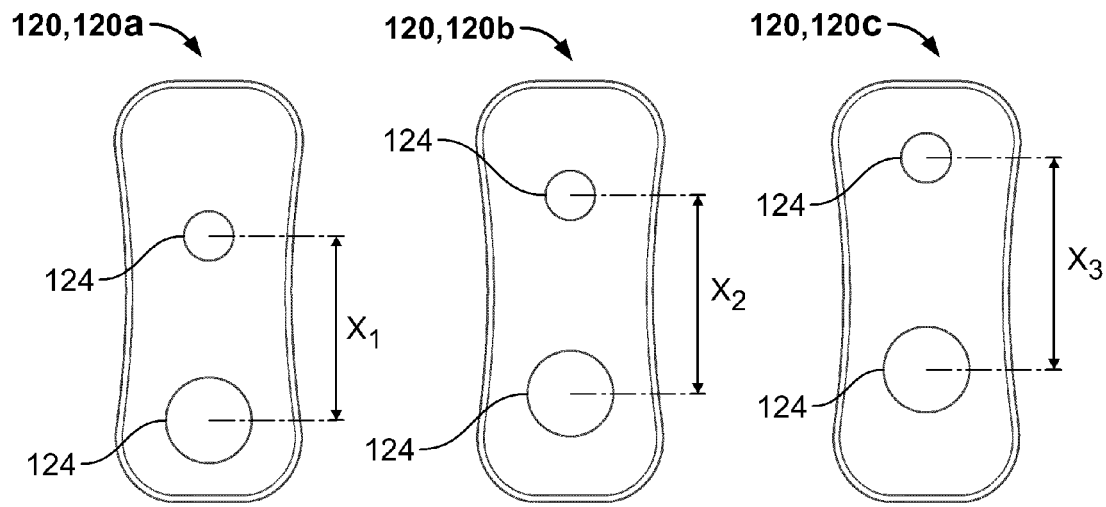
FIGS. 7B, 7C and 7D are plan views of exemplary drill templates according to the present teachings.

A femoral drill insert or femoral drill template 120 (120a, 120b, 120c) can be provided for guiding a drill to form one or more holes in the bone as determined during the preoperative plan for a preoperatively-selected implant size. Exemplary femoral drill templates 120 are illustrated in FIGS. 7B-D, 8 and 8A. Each femoral drill template 120 can be in the form of an insert with an outer tapered peripheral wall 122 that can mate with the inner tapered peripheral wall 110 of the elongated slot 106, shown in FIG. 8, for registering with the partial femoral alignment guide 100. Each femoral drill template 120 can include a number of guiding holes 124 of different sizes (diameters) and spacing at a patient-specific location and configuration relative to the femoral alignment guide 100. Two guiding holes 124 with different sizes and spacing ($X_1$, $X_2$, $X_3$) are illustrated in FIGS. 7B-7D. Depending on the procedure, the surgeon can determine intraoperatively which femoral drill template 120 to use and where to drill corresponding holes 86 in the bone for supporting a resection block 150, as shown in FIG. 3.

In some embodiments, several patient-specific femoral drill templates 120 having different configurations of guiding holes 124 can be provided for intraoperative selection and intraoperative change of implant sizing. For example, the femoral drill template 120b of FIG. 7C having a spacing or distance (measured center to center) $X_2$ between guiding holes 124 can be provided for the preoperative selected implant size. Intraoperatively, the surgeon may downsize the implant and select the femoral drill template 120a of FIG. 7B, which has a spacing $X_1$ that is smaller than $X_2$. Similarly, the surgeon may increase the size of the implant and select the femoral drill template 120c of FIG. 7D, which has a spacing $X_3$ that is greater than $X_2$. Accordingly, three femoral drill templates can be provided for a non-custom implant in a patient-specific kit that includes a patient-specific alignment guide to cover the size of the preoperatively selected implant and the two adjacent sizes, one above and one below the size of the preoperatively selected implant. Having femoral drill templates 120 for three different implant sizes, allows the surgeon to use the patient-specific femoral alignment guide 100 even when the size of the implant is changed intraoperatively. The femoral drill templates 120 can be metallic and reusable, although plastic or partially plastic drill templates with sufficient thickness to provide stability can also be used.

Figure 8:
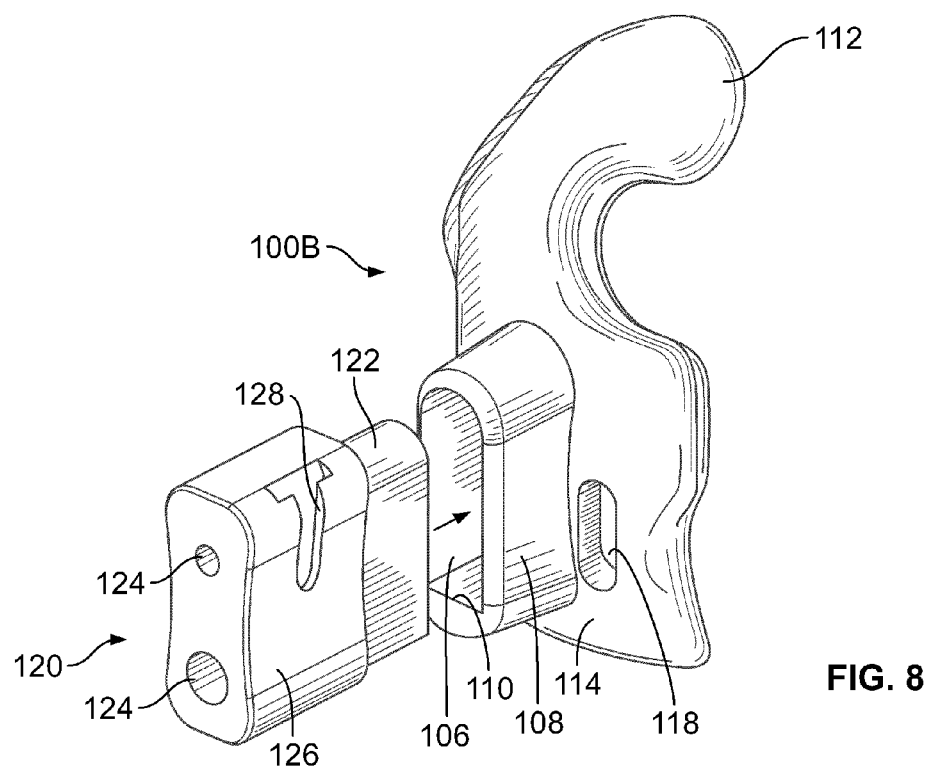
FIG. 8 is a perspective view of a femoral drill template for use with a patient-specific partial femoral alignment guide according to the present teachings.
Figure 8A:
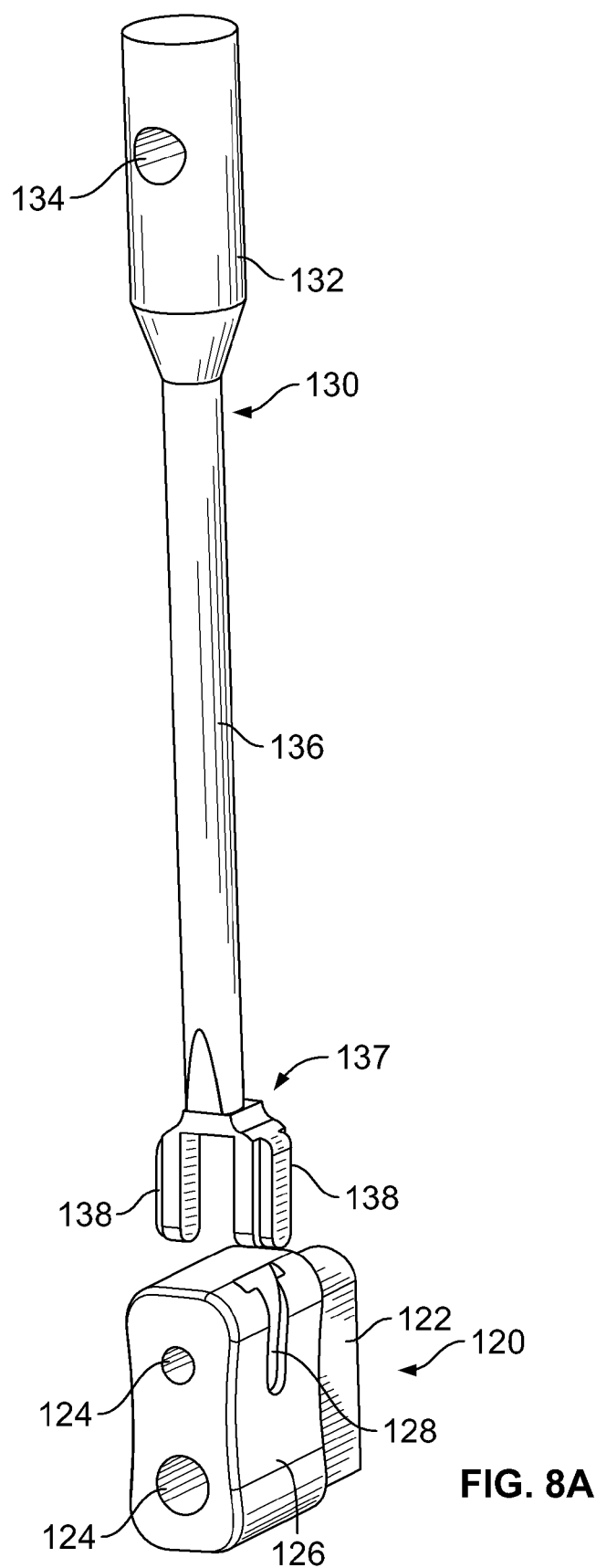
FIG. 8A is a perspective view of the femoral drill template of FIG. 8 shown with an alignment verification instrument according to the present teachings.

Referring to FIGS. 8 and 8A, the femoral drill template 120 can include a block portion 126 having an engagement feature, such as one or two outer slots 128 on opposite sides of the block portion 126, for coupling with a femoral alignment verification instrument 130, as shown in FIG. 8A. The alignment verification instrument 130 can include a proximal portion 132 with an opening 134 for an extramedullary rod (not shown), an elongated shaft 136 and a distal portion 137 that bifurcates into two fingers 138. In some embodiments, each finger 138 can engage a corresponding slot 128 on opposite sides of the block portion 126. In other embodiments, the block portion 126 has a single slot 128 such that one finger 138 engages the single slot 128 and the other finger 138 is held against the opposite side of the block portion 126. When the femoral drill template 120 is inserted into the slot 106 of the partial femoral alignment guide 100 and the alignment verification instrument 130 is coupled to the femoral drill template 120, the extramedullary rod can verify alignment of the guiding holes 124 relative to the mechanical axis of the leg of the patient.

Intraoperatively, the surgeon can mount the partial femoral alignment guide 100 on the specified knee and condyle of the patient in a unique position based on the preoperative plan for the patient. If the surgeon determines to proceed with the partial knee procedure and the preoperatively-selected implant, then the drill template 120b can be fitted over the elongated slot 106 and holes 86 for guiding pins can be drilled into the femoral bone 80. If the surgeon changes the size of the implant intraoperatively, the one of the other femoral drill templates 120a, 120b can be used, as discussed above. After corresponding holes 86 are drilled in the femoral bone 80, the partial femoral alignment guide 100 can then be removed, and the holes 86 can be used to mount rods or pins 152 of a cutting instrument, such as the resection block 150 illustrated in FIG. 3, in a position predetermined by the holes 86 drilled in the bone. The resection block 150 can be positioned over the pins 152 for performing a resection along a plane 88 for excising the posterior facet of the femoral condyle at a location and orientation determined during the preoperative plan for the patient. The surgical technique can then follow standard procedures, such as, for example, the surgical technique associated with the Oxford® Partial Knee, which is commercially available by Biomet Manufacturing Corp., Warsaw, Ind., and described at Biomet's website.

Figure 10:
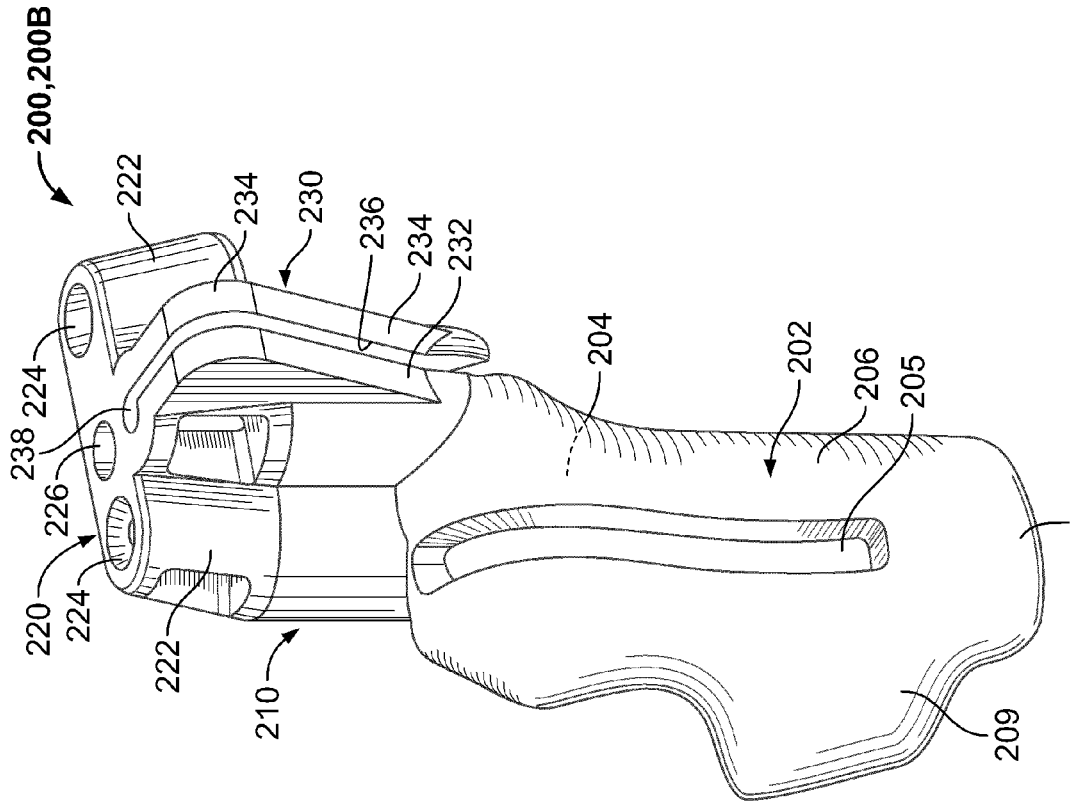
FIGS. 10 and 10A are perspective views of another patient-specific partial tibial guide according to the present teachings.
Figure 11:
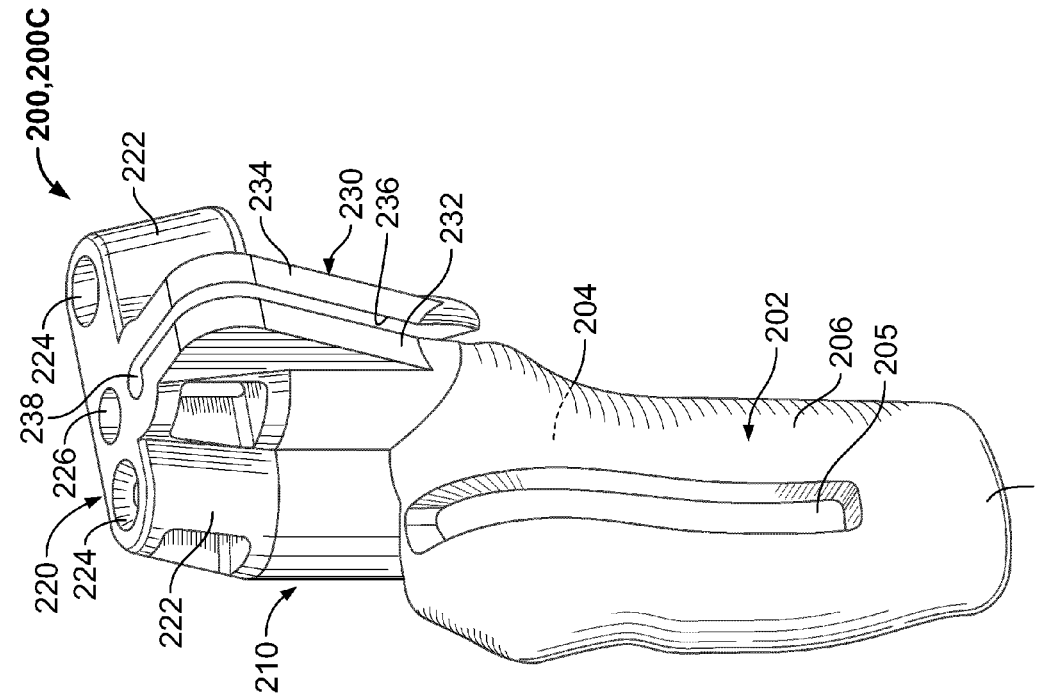
FIG. 11 is a perspective view of another patient-specific partial tibial guide according to the present teachings.
Figure 12:
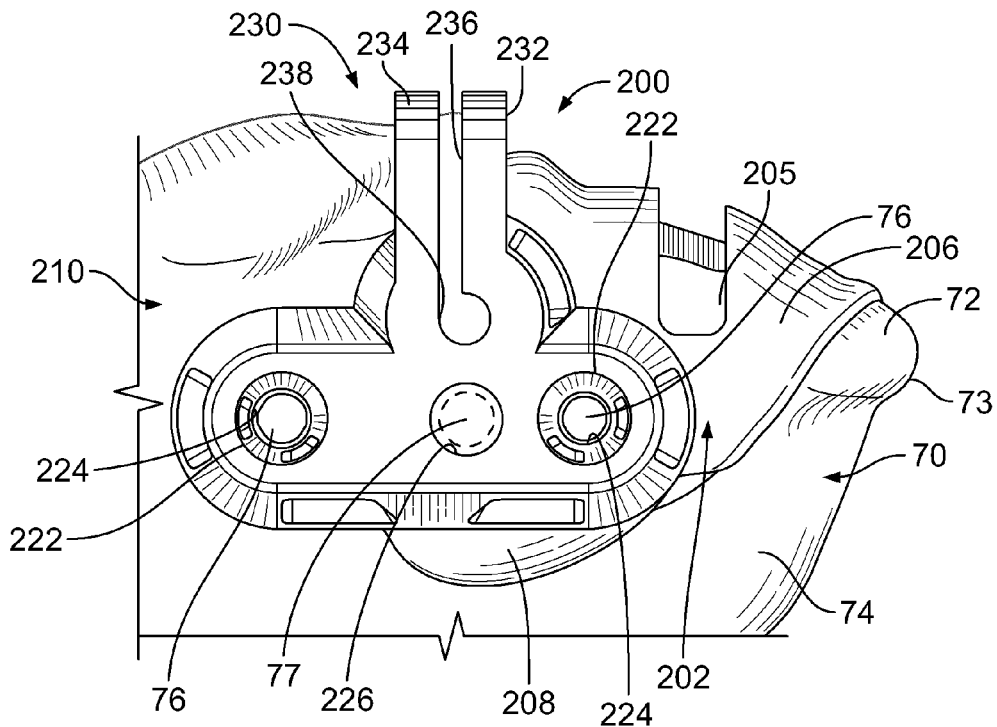
FIG. 12 is an environmental view of the patient-specific partial tibial guide of FIG. 9.
Figure 13:
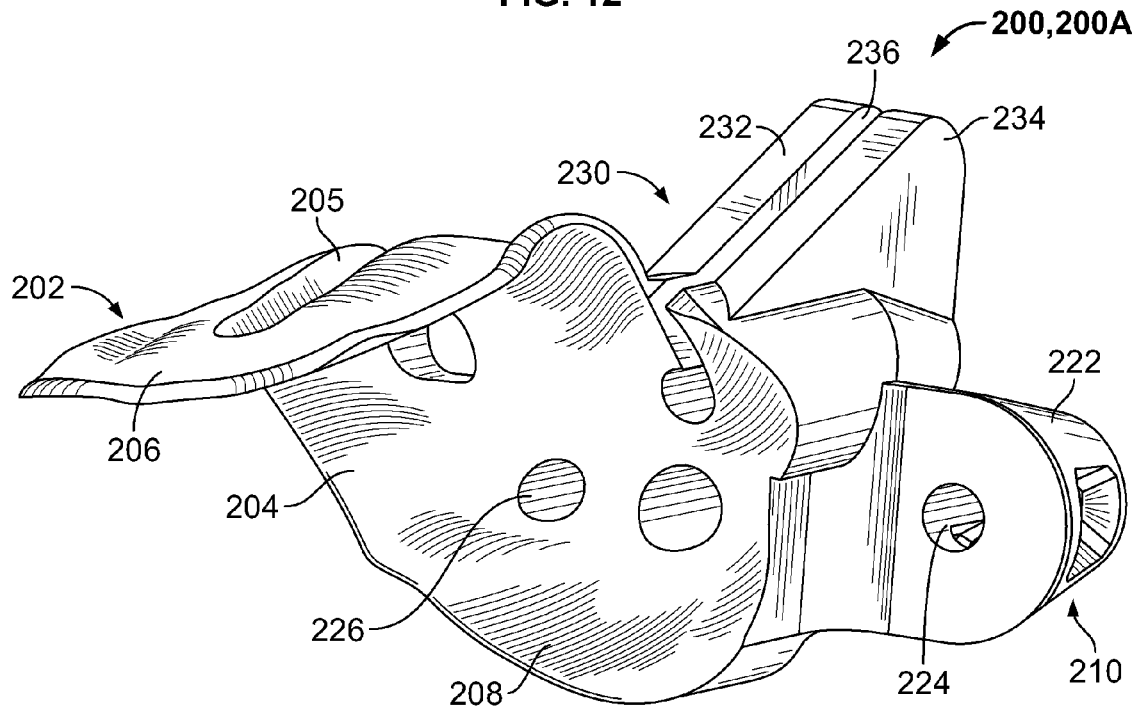
FIG. 13 is another perspective view of the patient-specific partial tibial guide of FIG. 9.

Referring to FIGS. 9-15, various partial tibial guides 200 (200A, 200B, 200C) and related instruments for partial or unicompartmental (or unilateral) arthroplasty including the tibia are described. The partial tibial guide 200 includes a patient-specific body 202 having a patient-specific undersurface or inner surface 204 designed during the preoperative plan to conform to unilaterally, i.e., to only one of the medial and lateral (proximally and anteriorly) regions the tibial bone 70 (either with or without articular cartilage) of the patient in only one position, as shown in FIG. 12. The patient-specific body 202 includes a proximal portion 206 engageable with a surface of a proximal plateau 72 of the tibial bone 70 and an anterior portion 208 engageable with an anterior surface 74 of the tibial bone 70. The patient-specific body 202 can include a window 205 in the form of an elongated slot. The partial tibial guide 200 is illustrated on a medial side of the right knee in the embodiment of FIG. 12.

With continued reference to FIGS. 9-15, the partial tibial guide 200 includes a drill/resection portion or block 210 that is integrally or monolithically attached to the patient-specific body 202 and includes a drill guide portion 220 and a resection guide portion 230. The drill guide portion 220 includes first and second registration formations 222 in the form of tapered tubular cones with tapered bores 224 for registration with a tibial drill template (or tibial drill insert) 300 shown in FIG. 15. The tapered bores 224 of the drill guide portion 220 are configured to receive corresponding first and second registration formations 304 (also in the form of tapered tubular registration cones) of the tibial drill template 300. The tibial drill template 300 includes first and second bores 306 passing through the corresponding first and second registration formations 304. When the tibial drill template 300 is mounted on the drill guide portion 220 of the partial tibial guide 200, their corresponding bores 306 and 224 are coaxially aligned for guiding a drill bit to drill corresponding holes on the tibial bone 70. Further, the drill guide portion 220 includes a cylindrical clearance bore or hole 226 configured to receive and provide clearance for a corresponding cylindrical tubular shaft 308 of the tibial drill template 300. The first and second or outer bores 306 of the tibial drill template 300 and the first and second or outer bores 224 of the drill guide portion 220 of the partial tibial guide 200 are configured for registering the tibial drill template 300 to the partial tibial guide 200, such that corresponding first and second or outer tibial holes 76 (shown in FIG. 12) can be drilled into the tibial bone 70. A third or middle bore 310 is formed through the tibial drill template 300, passes through the middle tubular shaft 308 and is coaxial with the clearance hole 226 of the drill guide portion 220 so that a third or middle hole 77 can be drilled into the tibial bone. The two outer bores 306 and the middle bore 310 are positioned and spaced relative to the tibial drill template 300 to allow a non-custom tibial resection block 400 to be supported on pins 420 received in either the outer holes 76 or in the middle hole 77 and the outer hole 76 located medially to the middle hole 77 to perform a horizontal resection after a vertical resection of the tibial bone is completed, as discussed below in reference to FIGS. 16 and 17. The choice of which two holes are used depends on the available tibial resection block 400, although a tibial resection block having predrilled holes for both options can also be provided.

With continued reference to FIGS. 9-15, the resection guide portion 230 of the partial tibial guide 200 includes a vertical resection slot 236 for a vertical resection, i.e., a resection parallel to the direction of gravity when the partial tibial guide 200 is mounted on the patient's tibial bone. The vertical resection slot 236 can be formed between first and second parallel planar (and vertical) resection flanges 232, 234 that extend from the block 210 of the partial tibial guide 200 and are located between the first and second registration formations 222 relative to the drill guide portion 220. A rounded hole (safety stop hole) 238 is formed at the bottom end of the vertical resection slot 236 and forms a safety stop for the vertical resection of the tibial bone 70. Specifically, a stop pin (not shown) can be inserted into the safety stop hole 238 to limit the depth of the vertical resection and prevent overresection through the vertical resection slot 236.

Referring to FIGS. 14 and 15, the tibial drill template 300 can also include first and second opposing slots 320 on opposite outer sides of the tibial drill template 300 for engaging a tibial alignment verification instrument 350. The first and second slots are substantially perpendicular to the longitudinal axes of the first and second bores 306. The tibial alignment verification instrument 350 includes an elongated shaft 352 having a bifurcated proximal end 354 with first and second arms 356 that can engage the first and second slots 320 of the tibial drill template 300. The first and second arms 356 can have a T-shaped or dovetail shape cross-section corresponding to similar cross-sections for the first and second slots 320. The shaft 352 can have a distal end 358 in the form of a plate or flange extending at an angle from the shaft 352 and having an opening 360 for receiving an extramedullary alignment rod (not shown). When the partial tibial guide 200 is mounted on the tibial bone 70 and coupled to the tibial drill template 300, the tibial alignment verification instrument 350 can be coupled to the tibial drill template 300, as discussed above to verify the alignment for the partial tibial guide 200 before drilling holes through the tibial bone 70.

Figure 9:
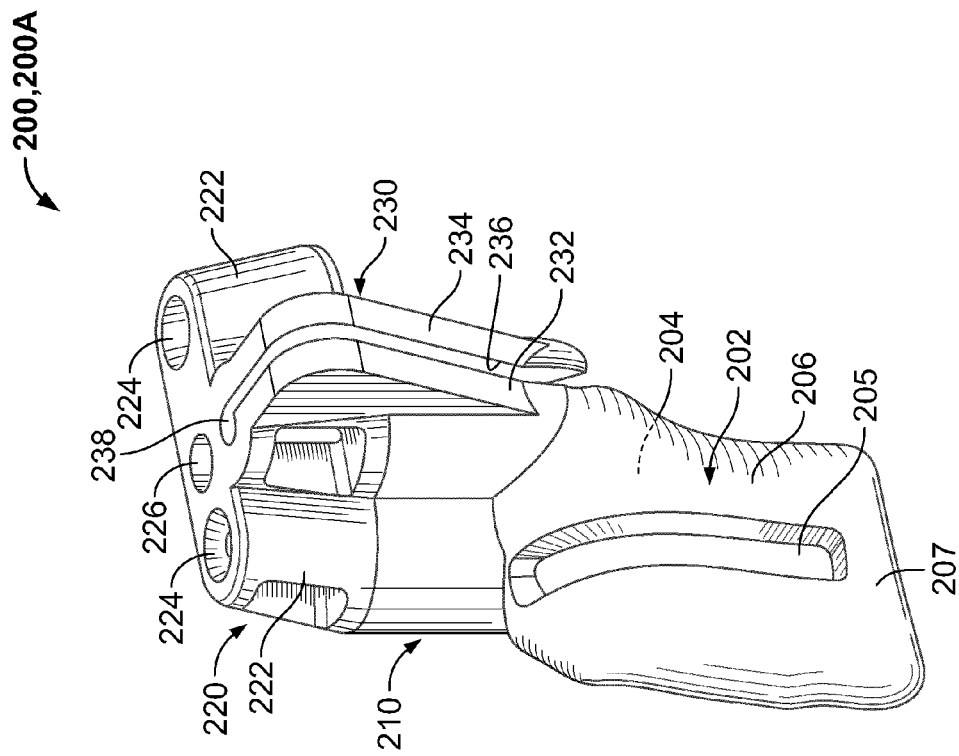
FIG. 9 is a perspective view of a patient-specific partial tibial guide according to the present teachings.
Figure 10A:
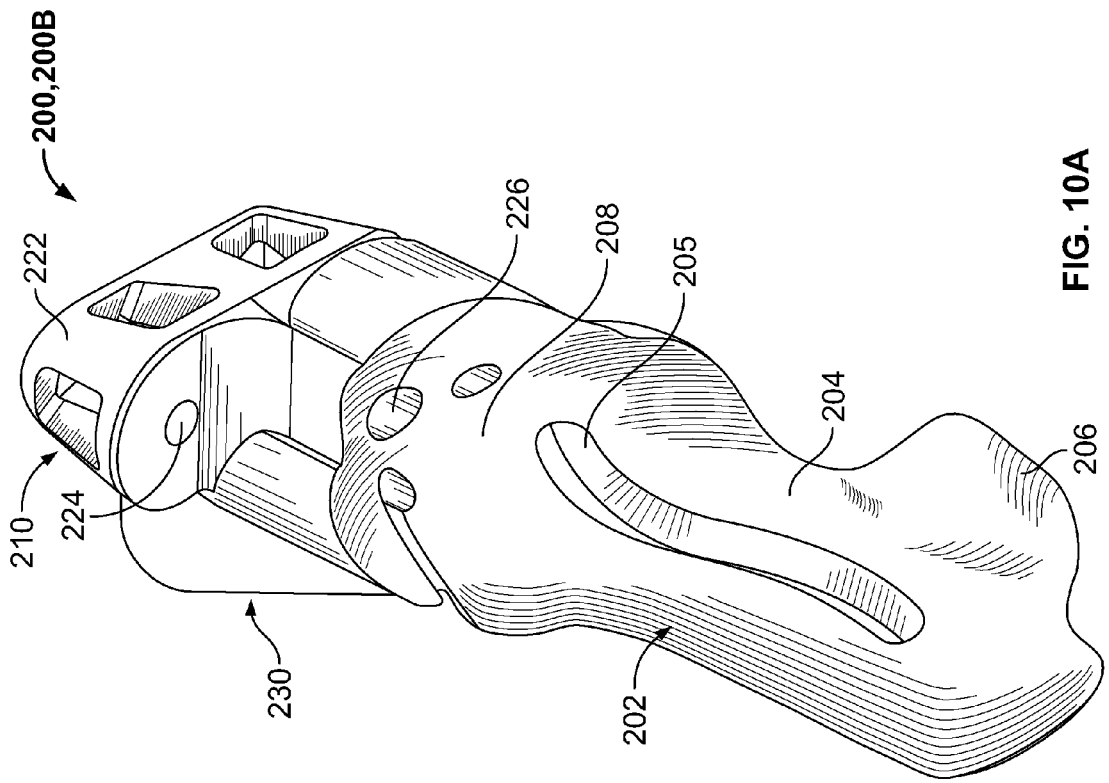

Referring to FIGS. 9-11, three variations of the partial tibial guide 200 are illustrated. As compared to the embodiment 200A shown in FIG. 9, the embodiment 200C of FIG. 11 corresponds to an instrument of greater size having longer overall dimensions, a longer patient-specific body 202 with a longer window 205 and including a longer or extended posterior segment 207. The longer posterior segment 207 provides additional coverage over the posterior portion of the proximal plateau 72 of the tibial bone 70. The embodiment 200B shown in FIGS. 10 and 10A also includes an extended posterior segment 207 in the patient-specific body 202 and additionally a medial clip-like flange 209 configured to wrap around and lock with a corresponding ridge 73 (ridge 73 is shown in FIG. 12) of a medial side of the proximal plateau 72 of the tibial bone 70.

Figure 16:
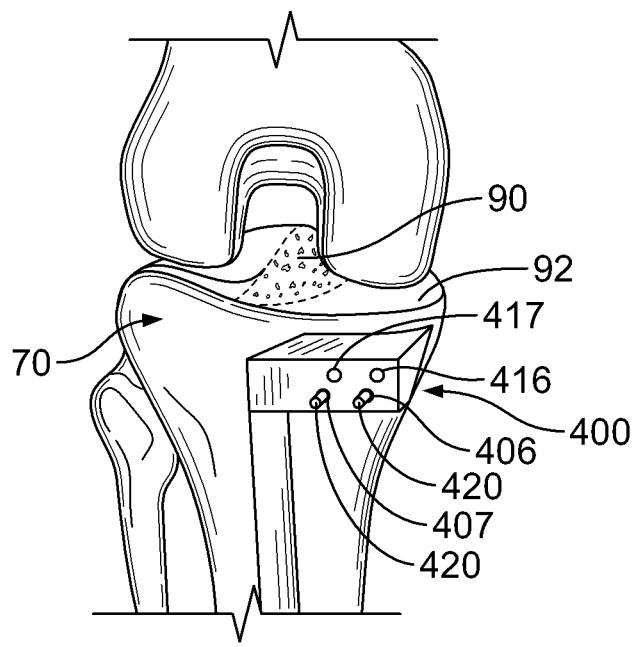
FIG. 16 is an environmental view of a tibial cutting block mounted on anterior pins on the tibial bone after a vertical resection made according to the present teachings.
Figure 17:
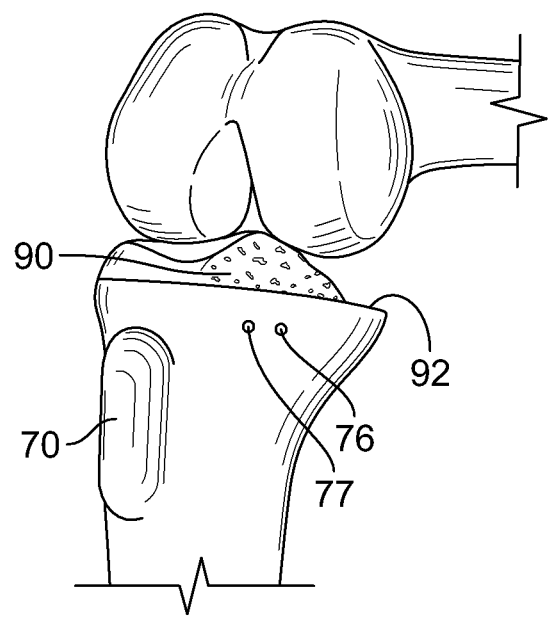
FIG. 17 is a perspective view of a tibial bone after vertical and horizontal resections are made according to the present teachings.

Referring to FIGS. 12, 14-17, after the vertical resection 90 of the proximal medial tibial plateau of the tibial bone 70 is made with a cutting tool guided by the vertical resection slot 236 of the partial tibial guide 200, the partial tibial guide 200 and the tibial drill template 300 are removed. Additionally, the pin passing through the safety stop hole 238 and another anterior pin is removed, leaving in the tibial bone 70 with two anterior pins 420 corresponding to the outer holes 76 or to the middle hole 77 and the outer hole 76 that is medial to the middle hole 77, as shown in FIGS. 16 and 17, depending on the type of the tibial resection block 400 that is used for performing the horizontal resection 92 and removing the proximal medial tibial plateau, as shown in FIG. 17. The tibial resection block 400 shown in FIG. 16 includes a pair of holes 407, 406 corresponding to holes 77, 76 shown in FIGS. 17 and 12, as discussed above. The tibial resection block 400 can include another pair of holes 417, 416 providing an intraoperative choice for selecting the depth of resection. The exposed vertical resection face 90 and the exposed horizontal resection 92 are shown in FIG. 17, after the tibial resection block 400 and the supporting anterior pins 420 are removed.

Summarizing, the present teachings provide various patient-specific unicompartmental alignment and resection guides, drill templates or drill inserts and other instruments for partial knee arthroplasty including the femoral and tibial bones. Further, the instruments provided can be used to perform first a vertical resection of the proximal medial tibial plateau followed by a horizontal resection to remove the proximal medial tibial plateau in preparation of a unicompartmental tibial implant. Additionally, instruments for intraoperative verification of alignment in cooperation with the patient-specific unicompartmental alignment and resection guides and drill templates. A surgical kit including patient-specific unicompartmental alignment and resections guides, drill templates, alignment verification instruments and corresponding custom or non-custom implants can be prepared for a specific patient and surgeon. Non-custom unicompartmental or partial knee implants are, for example, commercially available from Biomet Manufacturing Corp., Warsaw, Ind.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A surgical kit for unicompartmental knee arthroplasty comprising:
   a unitary patient-specific unicompartmental tibial guide comprising:
      a patient-specific body with an inner surface preoperatively configured to nestingly conform and mate in only one position with an anterior portion and a proximal portion of one compartment of a tibial bone of a specific patient;
      a drill guide portion positioned within the tibial guide body comprising first and second tubular bores preoperatively configured for receiving within the first and second tubular bores a drill for drilling first and second anterior holes into the tibial bone for guiding a horizontal tibial resection; and
      a vertical resection guide portion positioned within the tibial guide body comprising a vertical slot comprising an opening that extends vertically that is preoperatively configured for receiving within the vertical slot a cutting tool for guiding a vertical resection through the tibial bone before the horizontal tibial resection; and
   wherein the first and second anterior holes are drilled to receive a horizontal resection guide separate from the patient-specific unicompartmental tibial guide for guiding the horizontal tibial resection.

2. The surgical kit of claim 1, wherein the vertical resection guide portion includes first and second resection flanges forming the vertical resection slot.

3. The surgical kit of claim 2, wherein the vertical resection slot ends in a safety stop hole formed between the first and second resection flanges, wherein the safety stop hole is configured to receive a stop pin configured to limit a depth of the vertical resection.

4. The surgical kit of claim 1, wherein the drill guide portion includes first and second tapered bores configured for registration with a tibial drill template.

5. The surgical kit of claim 4, wherein the drill guide portion includes a third tapered bore.

6. The surgical kit of claim 1, wherein the patient-specific body includes a posterior segment configured to mateably engage a posterior portion of the proximal plateau of the tibial bone.

7. The surgical kit of claim 6, wherein the patient-specific body includes a flange configured to wrap around and lock with a corresponding ridge of a medial side of the proximal plateau of the tibial bone.

8. The surgical kit of claim 5, further comprising a tibial drill template having first and second tapered and tubular registration formations configured to be received in the first and second tapered bores of the drill guide portion of the tibial guide.

9. The surgical kit of claim 8, wherein the tibial drill template includes a tubular cylindrical shaft configured to be received into the third tapered bore.

10. The surgical kit of claim 8, wherein the tibial drill template includes first and second outer slots for engaging an alignment verification instrument.

11. The surgical kit of claim 10, further comprising an alignment verification instrument having a bifurcated distal end engaging the outer slots of the tibial template and a proximal end having an opening for guiding an extramedullary alignment rod.

12. The surgical kit of claim 1, further comprising: a unitary patient-specific unicompartmental femoral guide comprising: a patient-specific body with an inner surface preoperatively configured to nestingly conform and mate in only one position with an anterior portion and a distal portion of one compartment of a distal femoral bone of a specific patient, and an elongated slot opening through the femoral guide, the slot having a tapered inner wall.

13. The surgical kit of claim 12, further comprising a femoral drill template having a tapered outer portion configured to be received in the elongated slot and first and second guiding holes configured for drilling holes into the femoral bone to support a resection block.

14. The surgical kit of claim 12, further comprising a plurality of femoral drill templates, each template having a tapered outer portion configured to be received in the elongated slot and first and second guiding holes configured for drilling holes into the femoral bone to support a resection block, wherein the first and second holes of each of the plurality of femoral drill templates has different spacing for each femoral drill template.

15. The surgical kit of claim 14, wherein the first and second holes of each femoral drill template have different sizes.

16. The surgical kit of claim 13, wherein the femoral drill template includes first and second outer slots for engaging an alignment verification instrument.

17. The surgical kit of claim 16, further comprising an alignment verification instrument having a bifurcated distal end configured to engage the outer slots of the femoral template and a proximal end having an opening configured for guiding an extramedullary alignment rod.

* * * * *